United States Patent [19]

Quentin-Millet et al.

[11] Patent Number: 4,774,086

[45] Date of Patent: Sep. 27, 1988

[54] PROCESS FOR THE PURIFICATION, SOLUBILIZATION AND/OR DETOXIFICATION OF PROTEIN ANTIGENS OF BACTERIA OF THE BORDETELLA GENUS USING A CARBONATE BUFFER AND AN ACELLULAR ANTI-WHOOPING COUGH VACCINE

[75] Inventors: Marie-José B. Quentin-Millet, Villeurbanne; François Arminjon, Lyons, both of France

[73] Assignee: Institut Merieux, Lyons, France

[21] Appl. No.: 38,749

[22] Filed: Apr. 15, 1987

[30] Foreign Application Priority Data

Apr. 16, 1986 [FR] France ............ 86 05456

[51] Int. Cl.[4] ............ A61K 39/10; C07K 3/20

[52] U.S. Cl. ............ 424/92; 435/243; 435/244; 435/253; 530/417

[58] Field of Search ............ 435/243, 244, 253; 530/417; 424/92

[56] References Cited

U.S. PATENT DOCUMENTS

| | | | |
|---|---|---|---|
| 4,247,452 | 1/1981 | Irons et al. | 424/92 X |
| 4,455,297 | 6/1984 | Syukuda et al. | 424/92 |
| 4,500,639 | 2/1985 | Suzuki et al. | 435/243 X |
| 4,551,429 | 11/1985 | Greenspan | 424/92 X |
| 4,563,303 | 1/1986 | Ginnaga et al. | 530/417 |
| 4,687,738 | 8/1987 | Ginnaga et al. | 424/92 X |
| 4,704,274 | 11/1987 | Sakuma et al. | 424/92 X |
| 4,705,686 | 11/1987 | Scott et al. | 424/92 |

FOREIGN PATENT DOCUMENTS

| | | |
|---|---|---|
| 0077646 | 4/1983 | European Pat. Off. . |
| 0140386 | 5/1985 | European Pat. Off. . |
| 0162639 | 11/1985 | European Pat. Off. . |
| 2047886 | 3/1971 | France . |

OTHER PUBLICATIONS

Vaccine, vol. 3, (1985), Robinson et al., pp. 11-22.
The Lancet, Jan. 21, 1984, Sato et al., pp. 122-126.
Infection and Immunity, 41 (1983), Sato et al., pp. 313-320.

*Primary Examiner*—Howard E. Schain
*Attorney, Agent, or Firm*—Cushman, Darby & Cushman

[57] ABSTRACT

A method for the purification, solubilization and/or detoxification of protein antigens of bacteria of the Bordetella genus involves the use of a carbonate buffer having a pH of 8.3 to 11.6. An acellular anti-whooping cough vaccine containing active principles in this carbonate buffer is also disclosed.

16 Claims, No Drawings

PROCESS FOR THE PURIFICATION, SOLUBILIZATION AND/OR DETOXIFICATION OF PROTEIN ANTIGENS OF BACTERIA OF THE BORDETELLA GENUS USING A CARBONATE BUFFER AND AN ACELLULAR ANTI-WHOOPING COUGH VACCINE

The present invention relates to a process for purifying protein antigens of bacteria belonging to the Bordetella genus so as to obtain an acellular vaccine.

It is known that the culture of bacteria of the Bordetella genus, for example, *Bordetella pertussis, Bordetella parapertussis* and *Bordetella bronchiseptica* produces the F-HA protein (Filamentous Hemagglutinin); also, the culture of *B. pertussis* yields an exotoxin protein: pertussis toxin (also called LPF or LPF-HA: Leukocytosis Promoting Factor-Hemagglutinin).

The bacteria of the Bordetella genus are known pathogen agents. It is known in particular that *Bordetella pertussis* bacterium is the pathogen agent of whooping cough and that its industrial culture is used in the production of an anti-whooping cough vaccine.

It is also known that the pertussis toxin antigens and F-HA are usefully employed in an acellular anti-whooping cough vaccine composition.

The purification of the pertussis toxin comprises generally an affinity chromatography purification step.

The elution of the pertussis toxin from an affinity chromatography support is generally carried out using buffers containing, in high concentrations, salts and/or chaotropic agents or denaturants such as magnesium chloride, urea, sodium or potassium thiocyanate, guanidine hydrochloride and the like. However, the active principle recovered in th presence of these products cannot be used, as such, in a vaccinal preparation. Consequently, the eluate containing the toxin must undergo a supplemental treatment having for a purpose the complete removal of the chaotropic agents and/or the reduction of the saline concentration. This supplemental treatment can comprise, for example, an exhaustive diaylsis or gel filtration; see for example U.S. Pat. No. 4,500,639 and European Patent Application No. 0140386.

Moreover, the use of these elution techniques involves generally a partial and irreversible insolubilization of the active principle.

The present invention relates to the use of a particular buffer solution which permits the purification of the pertussis toxin. The use of this particular buffer of the present invention permits the elution of the pertussis toxin from the affinity chromatography support. The use of this buffer provides the elution and purification of the pertussis toxin in a single step and in high yields. The use of this same buffer, to which is added a surfactant, also permits the solubilization, without loss, of the pertussis toxin and F-HA. This buffer also serves as the solvent in the detoxification of the pertussis toxin and maintains the anatoxin in solution.

Moreover, contrary to conventionally employed buffers, the particular buffer of the present invention is compatible with the preparation of a vaccine. In other words, the antigens in solution in this buffer can be used directly in a vaccinal preparation.

The present invention thus relates to the use, in the purification, the solubilization and/or the detoxification of pertussis toxin and F-HA bacteria of the Bordetella genus, of a carbonate buffer having a pH of 8.3 to 11.6. Such a buffer can be obtained in a known manner, for example, by making an aqueous solution of a mixture of alkali metal bicarbonate (hydrogencarbonate) and an alkali metal carbonate (the alkali metal being sodium or potassium) or even by mixing in an aqueous solution an alkali metal bicarbonate and an alkali metal (sodium or potassium) hydroxide.

Preferably, the carbonate buffer has a molarity of 0.025–0.5 M, and a pH of 8.3 to 11.6.

The carbonate buffer employed in the present invention can also contain a surfactant, for example, a non-ionic surfactant such as TWEEN 80 (commercial designation of sorbitan mono oleate polyoxyethylenated with 20 moles of ethylene oxide).

As a general rule, a buffer with a surfactant is preferably employed when it is necessary to dissolve the product (pertussis toxin or F-HA) provided in the form of a precipitate or lyophilizate. The concentration of the surfactant in the buffer is generally less than 1 percent by weight, and most often less than 0.5 weight percent. When it is a question of eluting the pertussis toxin the carbonate buffer without the surfactant is preferably employed.

The use, in accordance with the present invention, of such carbonate buffers provides the following described advantages.

The carbonate buffer permits the elution of the pertussis toxin from an affinity chromatography support. The liquid to be chromatographed can be either a bacteria culture supernatant of the Bordetella genus, or a fraction enriched in pertussis toxin.

It is known that the use of pertussis toxin in an acellular vaccine requires a previous detoxification operation, for example, by treatment with formol or glutaraldehyde. The detoxification has for a purpose the removal principally of the induction effect of mice lymphocytosis, the sensitization to histamine, the ADP-ribosyl transferase activity, the cytopathogen effect on CHO cells (Chinese Hamster Ovary) and the like.

Such a detoxification, for example, using formol leads to an insolubilization of the toxin which makes it difficult to obtain a purified homogeneous preparation; see for example U.S. Pat. No. 4,455,297.

The use of the carbonate buffer of the present invention to which, optionally, has been added a surfactant, effects the detoxification operation in solution and maintains the resulting anatoxin in solution.

Finally, as indicated above, the solution of pertussis anatoxin in the carbonate buffer of the present invention can be used directly in an acellular vaccine preparation.

It has also been discovered that the carbonate buffer (to which, optionally a surfactant has been added, for example a non-ionic surfactant such as Tween 20) favors or improves the solubilization of F-HA.

The present invention also relates to a process for purifying protein antigens produced in the culture medium of Bordetella genus bacteria, this process comprising contacting the culture supernatant, or a fraction enriched in pertussis toxin, with a solid chromatography support, capable of fixing the pertussis toxin, and eluting the toxin from said solid support with a carbonate buffer having a pH of 8.3 to 11.6. If desired, the eluate can be submitted to a detoxification operation.

In a particular embodiment of the present invention, after having adjusted the pH to a value between 6 and 8, preferably to 7, the culture supernatant, or the fraction enriched in pertussis toxin, is contacted with a glycoprotein which has an affinity for the pertussis toxin, in particular with an asialoglycoprotein (asialofetuin, for example) coupled to a solid chromatography support. The amount of chromatography support employed is a function of the volume of starting solution and/or the pertussis toxin concentration in the fraction to be purified. Contact is made, for example, at a column temperature of 2° to 30° C.

The glycoproteins having an affinity for pertussis toxin are known. Representative ones include, for example, haptoglobin, fetuin and the like. However, the affinity chromatography is preferably carried out on proteins previously submitted to a desialylation treatment, this desialylation treatment being carried out by mild acid hydrolysis, in accordance with known methods; see for example Spiro et al, J. Biol. Chem. 1974, 249, 5704–5717.

The coupling of the glycoprotein or the desialyled glycoprotein can be carried out in accordance with known methods. The support can be any known solid support conventionally employed in affinity chromatography.

The support is principally a polyosidic derivative such as a cellulose derivative, crosslinked dextran, agarose gel on Sepharose-4B, or even a support based on acrylic derivatives such as "Trisacryl" sold by IBF (Industrie Biologique Franscaise).

The glycoprotein can be fixed on the support by using for example a support activated with CNBr.

The support can also be a porous silica support coated with crosslinked DEAE dextran. For example, Spherosil coated with DEAE dextran can be used.

The carbonate buffer employed in the process of the present invention is preferably a buffer having molarity of 0.025M to 0.5M and a pH of 8.3 to 11.6.

After elution, the pertussis toxin can be precipitated by ammonium sulfate (50–80% of saturation) or submitted directly to a detoxification operation.

The resulting purified toxin can be preserved in the form of the ammonium sulfate precipitate or a lyophilizate. The precipitate or lyophilizate can be redissolved in a carbonate buffer having a molarity greater than 25 mM and a pH from 8.3 to 11.6, which can contain a detergent such as Tween 80 at a final concentration of about 0.05–0.5 weight percent, preferably a 100 mM carbonate buffer having a pH of 9.6 containing 0.05 weight percent Tween 80 (hereinafter called CTW buffer).

In order to remove residual ammonium sulfate or the lyophilization support, the solution is dialyzed against several volumes of the same buffer, at a temperature from 2° to 30° C. for a period of time between 4 and 72 hours. The composition of the buffer provides total solubilization. The solution can be filtered on a membrane having a porosity of 0.22 μm. This provides the advantage of being able to proceed to the steps of detoxification in a sterile medium and to carrying out chemical or biologic experiments whose operation requires or is facilitated by complete dissolution of the active principle.

The optional detoxification of the pertussis toxin is carried out in a manner similar to that employed for toxins in general. In accordance with another aspect of the present invention, the detoxification operation is carried out in a carbonate buffer, such as defined above, containing preferably a surfactant which favors both the solubilization of the toxin and its maintenance in solution during the course of the detoxification reaction. The yield of the detoxification steps is thus near to 100%. The detoxification agents employed are for example formol or glutaraldehyde.

After detoxification, which can be carried out for example at a temperature of 4°–40° C., the solution containing the anatoxin can be dialyzed against the CTW buffer in order to remove all traces of detoxification agent. The resulting anatoxin remains in solution. It can be filtered on a sterile membrane having a porosity of 0.22 μm and is ready to be included in a vaccinal preparation.

As indicated above, the carbonate buffer described for use in the present invention also permits the complete solubilization of another protein isolated from the culture supernatants of bacteria of the Bordetella genus, i.e. F-HA. The use of this buffer in the solubilization of F-HA provides the advantages described in the case of the pertussis toxin, i.e., principally of being able to proceed to a sterilizing filtration step on a membrane having a porosity of 0.22 μm without loss of active principle. Under this form the F-HA can be directly included in a vaccinal preparation.

For example, the F-HA preserved in the form of an ammonium sulfate precipitate is solubilized in accordance with the technique previously described for pertussis toxin. The precipitate is centrifuged, taken up in CTW buffer and dialyzed at ambient temperature or at a temperature of 4°–8° C. for 4 to 72 hours. The CTW buffer provides the complete solubilization of the F-HA.

The present invention also relates to an acellular anti-whooping cough vaccine comprising at least one active principle selected from pertussis anatoxin and F-HA, the said active principle being dissolved in a carbonate buffer as described above, in particular in a carbonate buffer such as CTW containing a surfactant.

The pertussis anatoxin and the F-HA in solution in the carbonate buffer can be directly included in the vaccinal preparations which can contain either the anatoxin alone, or a mixture of the anatoxin and F-HA in the desired proportions. In order to correct the final pH of the vaccine to a value between 7 and 8, a certain volume of physiologic water buffered (PBS buffer) and acidified with a concentrated acid solution is added. The volume added is a function of the volume and the molarity of the carbonate buffer present in the preparation. The concentration of the active principle is then adjusted to the desired value by the addition of the necessary volume of PBS buffer. At this stage there can be added to the mixture other antigens (diptheria, tetanus, polio, hemophilia antigens), a preservative such as merthiolate or phenoxy ethanol and an adjuvant such as alumina gel or calcium phosphate.

The following non-limiting examples are given to illustrate the invention.

EXAMPLE 1

Purification of pertussis toxin by affinity chromatograph

(a) Adsorption of the pertussis toxin on the affinity support

A fraction enriched in pertussis toxin, obtained after centrifugation and concentration of a bacteria suspension of phase I *Bordetella pertussis*, cultivated in a fermentor of 30 liters, is passed through a column having a diameter of 4 cm containing 120 ml of Sepharose 4B chromatography support coupled to asialofetuin, at a flow rate of 6 ml/cm$^2$/hour.

The Sepharose 4-B was coupled to the asialofetuin in the following manner:

30 g of Sepharose 4-B activated with CNBr (Pharmacia) are swollen in 6 liters of 1 mM HCl for about 15 minutes. The gel is then washed three times with 6 liters of mM HCl. 400 ml of a solution containing 1 mg/ml of asialofetuin, 0.1M $NaHCO_3$ and 0.5M NaCl are added to the gel.

The mixture is left overnight to react at +4° C. with mild stirring. 125 ml of a 5M ethanolamine solution (pH=8.0) are added to the mixture. After 4 hours of incubation at ambient temperature, the gel is washed successively with 500 ml of 0.1M sodium acetate buffer (pH=4.0) containing 1M NaCl, then with 500 ml of 50 mM Tris- HCl buffer (pH=7.5) containing 1M NaCl. This washing cycle is repeated three times.

The gel is then washed three times with 500 ml of 50 mM Tris-HCl buffer (pH=7.5) in the presence of a preservative such as merthiolate at a concentration of 1/10,000 (w/v).

The asialofetuin employed as the ligand in the affinity chromatography was obtained in the following manner:

An aqueous solution of fetuin (type III fetuin, Sigma) is hydrolyzed by 0.05N $H_2SO_4$ for 1 hour at 80° C. After hydrolysis, the solution is dialyzed against several distilled water baths for 24 hours at +4° C. to remove free sialic acids. The asialofetuin solution can be concentrated by ultrafiltration using a system equipped with membranes whose cut-off threshold is equal to 10,000.

The removal of sialic acids is controlled by a specific colorimetric dosage of sialic acids on the protein, after and before hydrolysis.

(b) Elution of pertussis toxin

The gel is washed with two column volumes of 50 mM Tris-HCl buffer (ph=7.5), that is until complete disappearance of UV absorption at 278 nm, then with a column volume of 50 mM Tris-HCl buffer (ph=7.5) containing 1M NaCl. The pertussis toxin is eluted with 400 ml of 100 mM carbonate buffer (pH=9.6).

The carbonate buffer is prepared as follows: 500 ml of a 0.1M $NaHCO_3$ solution are added to a solution of 0.1M $Na_2CO_3$ until the final pH is 9.6. It is necessary to add about 250 ml of the $Na_2CO_3$ solution.

The resulting carbonate buffer is filtered on a membrane having a porosity of 0.22 μm and is preserved at +4° C.

The optical density and the hemagglutinating activity of the fractions collected at the exit of the column are measured.

The fractions containing the active principle, that is, the cells having strong hemagglutinating activity, non-inhibited by cholesterol, are combined.

The pertussis toxin is then precipitated by ammonium sulfate at a final concentration corresponding to 70% of saturation.

The thus purified pertussis toxin induces a strong lymphocytosis and sensitizes mice CFW to histamine at a dosage of 0.04 μg/mouse. The capacity for the toxin to induce the formation of clusters on CHO cells is characterized by a specific activity on the order of 65,000 to 260,000 CPU/μg.

The results of physico-chemical controls and biologic activities (colorimetric dosages of possible contaminants, DNA, RNA, sugar; dosage of the amount of endotoxin, electrophoresis in SDS medium or in acid medium, etc) are indicative of a final homogeneous preparation containing a highly purified active principle.

The analyses of the amount of pertussis toxin in the initial culture supernatant and in the final precipitate indicates a purification yield greater than 90%.

EXAMPLE 2

Comparative study of the dissolution followed by a sterilizing filtration of the pertussis toxin in various buffers.

1.2 ml of a suspension of pertussis toxin in the form of an ammonium sulfate precipitate at a concentration of 2.6 mg/ml are withdrawn and centrifuged for 10 minutes at 10,000×g. The supernatant is removed, the deposit taken up in 4 ml of CTW buffer and dialyzed against this same buffer. The toxin solution is filtered on a membrane having a porosity of 0.22 μm. The protein concentration of the solution, before and after filtration, is determined by a dosage according to the Lowry method and the results are expressed either as filtration yield: (toxin concentration after filtration/toxin concentration before filtration)×100, or relative percentage calculated with respect to the filtration yield in CTW buffer to which is arbitrarily assigned a yield of 100%.

The results are set forth in the following Table:

TABLE I

Comparative study of filtration yields of pertussis toxin in various buffers

| Buffer | Filtration Yield, % | Relative % with respect to CTW buffer |
|---|---|---|
| 20 mM sodium phosphate, 0.5 M NaCl, pH = 7.2 with 1% Zwittergent TM, 3-14 (N—tetradecyl N,N'—dimethyl-3-ammonio 1-propane sulfonate | 50 | 53 |
| 20 mM sodium phosphate, 0.5 M NaCl, pH = 7.2 with 3.5 × $10^{-6}$ M β-cyclodextrine | 34 | 36 |
| 20 mM sodium phosphate, 0.5 M NaCl, pH = 7.2 with 0.05% Tween 80 | 16 | 17 |
| 20 mM sodium phosphate, 0.5 M NaCl, pH = 7.2 with 1M urea | 37 | 39 |
| 100 mM citrate, pH = 7.0 | 25 | 27 |
| 100 mM carbonate, pH = 9.6 | 73 | 78 |
| CTW | 94 | 100 |

EXAMPLE 3

Detoxification of pertussis toxin

(a) Detoxification by formol 2 ml of a suspension of pertussis toxin, in the form of an ammonium sulfate precipitate, at a concentration of 5 mg/ml (or 10 mg of pertussis toxin) are centrifuged for 15 minutes at 10,000×g. The supernatant is removed and the deposit is taken up in 10 ml of CTW buffer.

The solution is dialyzed overnight at +4° C. against 2 liters of CTW buffer. On exit from the dialysis the solution is filtered on a membrane having a porosity of 0.22 μm. A dosage of proteins in accordance with the Lowry method is carried out on the filtered solution and the protein concentration is adjusted to 0.4 mg/ml, by the addition of CTW buffer. To 23 ml of solution of toxin at a concentration of 0.4 mg/ml, there are added 1.22 ml of 1M lysine in solution in CTW buffer and 0.265 ml of a 37% formol solution. The mixture is incubated, for example, for 21 days at 4° C. The reaction mixture is then dialyzed against the CTW buffer at +4° C. for 48 hours in order to remove all traces of formol. The anatoxin is then sterilely filtered on a membrane having a porosity of 0.22 μM. In this form the pertussis anatoxin can be incorporated in a vaccinal preparation.

(b) Detoxification by glutaraldehyde 15 ml of a solution of pertussis toxin at a concentration of 500 μg/ml in a CTW buffer are prepared as descibed above. 5 ml of a 0.10% glutaraldehyde solution in CTW buffer are added to the toxin solution.

The detoxification can be carried out at temperatures ranging from +4° C. to 40° C.; the toxin incubation period in the presence of glutaraldehyde is a function of the temperature. The mixture can be incubated for example for 48 hours at 4° C.

After incubation, 180 μl of 1M lysine in solution in the CTW buffer are added to the mixture and the solution is dialyzed for 48 hours at 4° C. against the CTW buffer. After dialysis, the pertussis anatoxin is filtered on a membrane having a porosity of 0.22 μm. In this form, it can be included in a vaccinal preparation.

EXAMPLE 4

Solubilization of F-HA by the carbonate buffer

The F-HA mentioned in these examples has been prepared in accordance with the procedures described in the publication of Y. Sato, J. L. Cowell, H. Sato, D. C. Burstyn and C. R. Manclark, entitled "Separation and Purification of the Hemagglutinins from *Bordetella pertussis*", Infect. and Immun., 1983, 41, 1,313,320.

The F-HA is preserved in the form of an ammonium sulfate precipate at 70% of saturation.

(a) 25 ml of a suspension of F-HA at a concentration of 1.2 mg/ml in the form of an ammonium sulfate precipitate are centrifuged for 20 minutes at 30,000×g. The supernatant is removed and the deposit is taken up in 30 ml of CTW buffer.

The solution is dialyzed overnight at +4° C. against CTW buffer. The solution is filtered on a membrane having a porosity of 0.22 μm. The F-HA can be incorporated, in this form, in a vaccinal preparation.

(b) A comparative study of the sterilizing filtration yields on a membrane having a porosity of 0.22 μm has been carried out.

450 μl of a suspension of F-HA precipitated with ammonium sulfate, at a concentration of 5.88 mg/ml, are retained and centrifuged for 10 minutes at 10,000×g. The supernatant is removed.

The deposit is taken up in 3 ml of buffer and dialyzed against this same buffer. The F-HA solution is filtered on a membrane having a porosity of 0.22 μm. The protein concentration of the solution, before and after filtration, is determined by a dosage in accordance with the Lowry method and the results are expressed either as filtration yields: (concentration after filtration/concentration before filtration)×100, or as a relative percentage calculated with respect to the filtration yield in CTW buffer to which is arbitrarily assigned a yield value of 100%.

The results are set forth in Table II below:

TABLE II

Comparative study of the filtration yields of F—HA in solution in various buffers.

| Buffer | Filtration Yield, % | Relative percent with respect to the CTW buffer |
|---|---|---|
| 0.1 M ammonium phosphate, pH = 4.5 | 54 | 61 |
| 0.1 M ammonium phosphate containing 0.5 M NaCl | 3 | 3 |
| 0.1 M ammonium phosphate with 0.05% Tween 80 | 72 | 81 |
| 0.1 M monopotassium phosphate, pH = 4.4 | 62 | 70 |
| 0.1 M monopotassium phosphate containing 0.5 M NaCl | 2 | 2 |
| 0.1 M monopotassium phosphate with 0.05% Tween 80 | 78 | 88 |
| 50 mM Tris-HCl, pH = 7.4 containing 0.5 M NaCl | 58 | 65 |
| CTW | 89 | 100 |

EXAMPLE 5

Preparation of an acellular pertussis vaccine

An acellular pertussis vaccine containing purified pertussis anatoxin and F-HA antigens can be prepared in the following manner:

The two antigens in solution in the CTW buffer are separately sterilized by filtration on a membrane having a porosity of 0.22 μm and their concentration is determined, for example, by colorimetric dosage in accordance with the Lowry method.

In order to prepare one liter of acellular pertussis vaccine containing 50 μg/ml of each of the active principles the following solutions are sterilely admixed:

| | |
|---|---|
| Solution of pertussis anatoxin at a concentration of 0.38 mg/ml in CTW buffer | 132 ml |
| Solution of F—HA at a concentration of 1.1 mg/ml in CTW buffer | 46 ml |
| Buffered physiologic water (PBS) containing 50 mM HCl | 202 ml |
| Aluminum hydroxide at a concentration of 10 mg of aluminum/ml | 20 ml |
| Merthiolate, 1% PBS (w/v) | 10 ml |
| PBS, sufficient amount for 1 liter. | |

This vacinal preparation exhibits the following characteristics.

| | |
|---|---|
| Pertussis anatoxin | 50 μg/ml |
| FHA | 50 μg/ml |
| Aluminum | 200 μg/ml |
| pH | 7.6 |
| Osmolality | 265 mosm/kg |
| Merthiolate | 1/10,000 |

What is claimed is:

1. A process for the purification of protein antigens produced in the culture medium of bacteria of the Bordetella genus comprising contacting the culture supernatant, or a fraction enriched in pertussis toxin, with a solid chromatography support capable of fixing the said pertussis toxin and eluting the said pertussis toxin from said solid support with a carbonate buffer having a pH ranging from 8.3 to 11.6.

2. The process of claim 1 wherein said carbonate buffer is a mixture of alkali metal bicarbonate and an alkali metal carbonate.

3. The process of claim 1 wherein said carbonate buffer has a molarity of 0.025 to 0.5M.

4. The process of claim 1 wherein said carbonate buffer also contains a surfactant in an amount less than 1 weight percent based on the total weight of said carbonate buffer.

5. The process of claim 1 which also includes detoxifying the pertussis toxin eluted from said solid support.

6. A process for solubilizing protein antigens produced in the culture medium of bacteria of the Bordetella genus comprising dissolving the said antigens, in the form of a precipitate or a lyophilyzate, in a carbonate buffer having a pH ranging from 8.3 to 11.6 to which has been added a surfactant in an amount less than 1 weight percent based on the total weight of said carbonate buffer.

7. The process of claim 6 wherein said carbonate buffer is a mixture of alkali metal bicarbonate and an alkali metal cabonate.

8. The process of claim 6 wherein said carbonate buffer has a molarity of 0.025 to 0.5 M.

9. A process for detoxifying pertussis toxin with a detoxification agent comprising detoxifying said pertussis toxin in a carbonate buffer having a pH ranging from 8.3 to 11.6.

10. The process of claim 9 wherein said carbonate buffer is a mixture alkali metal of bicarbonate and an alkali metal carbonate.

11. The process of claim 9 wherein said carbonate buffer has a molarity of 0.025 to 0.5 M.

12. The process of claim 9 wherein said carbonate buffer also contains a surfactant in an amount less than 1 weight percent based on the total weight of said carbonate buffer.

13. An acellular anti-whooping cough vaccine comprising a solution of an effective amount of at least one active principle selected from the group consisting of pertussis anatoxin and F-HA in a carbonate buffer having a pH ranging from 8.3 to 11.6.

14. The vaccine of claim 13 wherein said carbonate buffer is a mixture of alkali metal bicarbonate and an alkali metal carbonate.

15. The vaccine of claim 13 wherein said carbonate buffer has a molarity of 0.025 to 0.5M.

16. The vaccine of claim 13 wherein said carbonate buffer also contains a surfactant in an amount less than 1 weight percent based on the total weight of said carbonate buffer.

* * * * *